United States Patent [19]

Voege

[11] 4,241,896

[45] Dec. 30, 1980

[54] METHOD OF MAKING CALIBRATED GAS METERING ORIFICE AND PRODUCT THEREOF

[75] Inventor: Clayton B. Voege, Indianapolis, Ind.

[73] Assignee: Ray V. Bussell, Indianapolis, Ind.

[21] Appl. No.: 5,518

[22] Filed: Jan. 22, 1979

[51] Int. Cl.³ .......................... F16K 3/32; F16K 51/00
[52] U.S. Cl. .................................... 251/206; 251/208; 138/40; 29/525; 73/3
[58] Field of Search ...................... 251/205, 206, 208; 138/40, 45; 29/525, 157.1 R

[56] References Cited

U.S. PATENT DOCUMENTS

| 1,423,750 | 7/1922 | Brombacher . | |
|---|---|---|---|
| 1,982,754 | 12/1934 | Peterson | 251/206 X |
| 2,674,032 | 4/1954 | Martin et al. | 29/157 |
| 2,948,296 | 8/1960 | Thorburn | 137/517 |
| 2,980,392 | 4/1961 | Greenwood | 251/210 |
| 3,365,166 | 1/1968 | Smith | 251/121 |
| 3,949,966 | 4/1976 | Fabish | 251/206 |
| 3,995,356 | 12/1976 | Sheppard | 138/40 |
| 4,087,301 | 5/1978 | Steadman | 138/40 X |
| 4,157,808 | 6/1979 | Eidsmore | 251/121 X |
| 4,166,580 | 9/1979 | Meckel | 251/205 X |

*Primary Examiner*—Arnold Rosenthal
*Attorney, Agent, or Firm*—Jenkins, Coffey, Hyland, Badger & Conard

[57] ABSTRACT

A calibrated oxygen metering orifice for a portable oxygen supply kit is made by first forming a cylindrical hole in a valve body, then progressively pressing into the hole a plug of conforming cross section having in its surface a scored slot of progressively decreasing cross-sectional area which defines with the wall of the hole an orifice of a size depending on the depth to which the plug is inserted in the hole, monitoring the gas flow rate through such orifice as the plug is pressed into the hole, and stopping the plug at a position which gives the desired calibrated gas flow rate.

12 Claims, 11 Drawing Figures

METHOD OF MAKING CALIBRATED GAS METERING ORIFICE AND PRODUCT THEREOF

This invention relates to a method of making a calibrated gas metering orifice and to a gas metering device produced thereby. The invention is especially applicable to provide a precisely calibrated gas metering orifice for metering therapeutic oxygen flow in a portable oxygen supply kit adapted to be carried by an ambulatory patient to supply a prescribed rate of oxygen supply for such patient. The invention also relates to a selective control valve which uses such metering orifices to selectively provide a plurality of accurate oxygen flow rates.

Oxygen supply kits for ambulatory patients are known and in use. They include an indexing control valve which is movable to a plurality of positions, each providing a different flow rate, for example, one, two, three, four, and five liters per minute. Such flow rates are obtained by passing the gas at a regulated pressure through metering orifices in a metering disk. In one application, such rates required metering holes having diameters respectively of approximately 0.006, 0.009, 0.011, 0.013, and 0.015 inch. Heretofore, the orifices had been formed by drilling these small holes in the metering disk either mechanically or by an EDM process. Such drilling does not provide sufficient accuracy, and when the EDM process, which is the better of the two, is used, it is necessary to allow a margin of error of plus or minus 10% of the desired flow rate. The present invention provides a much more accurate metering orifice, and reduces the necessary margin of error to the order of plus or minus 1% or less.

In accordance with the invention, a calibrated gas metering orifice is formed by first forming a hole in a valve body, then progressively inserting into the hole, as by pressing with a press fit, a plug having in its surface a groove or other relief which opens through the entering end of the plug and is of progressively decreasing small cross-sectional area toward the opposite end of the plug, so that the groove forms with the wall of the hole an opening of a size which depends on the depth to which the plug is inserted in the hole. The gas flow rate through such orifice is monitored as the plug is pressed into the hole, and the plug is stopped at a position which gives the desired gas flow rate. The groove or relief on the surface of the plug is conveniently formed by scribing a progressively deepening notch axially along the surface of the plug and carrying the deep end of the notch through the end surface of the plug. The scribed groove should be of small cross-sectional area so as to include along its length one or more areas corresponding to the cross-sectional areas of round holes previously used as metering orifices. For example, a cross sectional area approximately equal to that of a 0.015 inch diameter hole is provided by a scribed V-shaped groove having a 60° included angle between its side walls and a depth of 0.010 inch. The groove should also have a relatively long taper so that its area varies at a slow rate lengthwise of the plug so that a fine adjustment can be produced as the plug is pressed into the hole. A V-shaped groove is desirable because its cross-sectional area varies linearly with its depth. However, other shaped grooves may be used. Also, the groove or relief might be made in the wall of the hole instead of the plug, and the plug formed with an uninterrupted surface. The resulting gas metering orifice comprises a valve body having a hole formed therethrough and a plug of conforming cross section inserted in the hole to a depth such that the groove formed at the interface between the plug and the hole wall defines an opening of a size which depends on the depth to which the plug is inserted in the hole, and with the plug inserted in the hole to a depth which produces an orifice size giving a desired gas flow rate.

The invention is especially useful in forming the very small orifices required for metering a gas such as oxygen at relatively low flow rates, such as orifices ranging in cross-sectional area from that of a 0.006 inch diameter hole (having an area of 0.0000282 square inch) up to say a 0.030 inch diameter hole (having an area of 0.0007 square inch).

In further accordance with the invention, a selective control valve is formed by providing a movable metering valve body with a plurality of such calibrated gas metering orifices and providing for movement of such valve body to bring such orifices selectively into position to control the flow of gas from an inlet to an outlet. Preferably, the valve body is in the form of a rotary disk, with the several orifices at angularly spaced positions on such disks, and the disk is mounted for rotation to selectively bring the several orifices into sealing engagement with a valve seat which defines the gas flow passage between the inlet and outlet of the control body. Preferably, the metering disk is mounted in a gas chamber and is spring-pressed axially into sealing engagement with a valve seat mounted in an end wall of such chamber. The disk may be loosely mounted on a rotary control hub, and may be supported at angularly spaced points by pressure pads carried by that same end wall, and rotation of the disks will bring any of the orifices selectively into operative relation with the valve seat so as to change the gas flow rate in accordance with that selection.

The accompanying drawings illustrate the invention and show a preferred embodiment which exemplifies the best mode of carrying out the invention as presently perceived. In such drawings.

Figure 1:
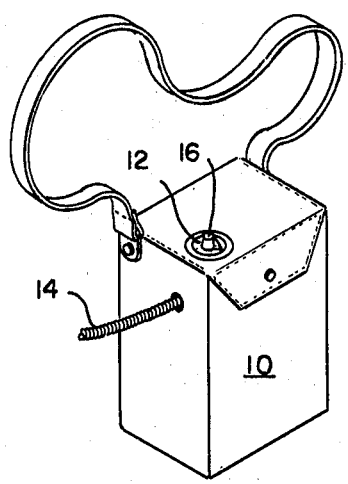
FIG. 1 is a perspective view of an oxygen supply kit adapted to be carried by an ambulatory patient.

The oxygen supply kit shown in FIG. 1 comprises a case 10 provided with a shoulder strap adapting it to be carried by an ambulatory patient. The case will include a suitable container of oxygen, a pressure regulator, a selective metering valve 12, and a supply tube 14 for conducting oxygen at the selected metered rate to a mask or other device for use by the patient. By way of example, the selective control valve 12 may supply oxygen at the rate of one, two, three, four, or five liters per minute, and the device is provided with an indexing knob 16 for selecting the rate prescribed by the doctor.

Figure 2:
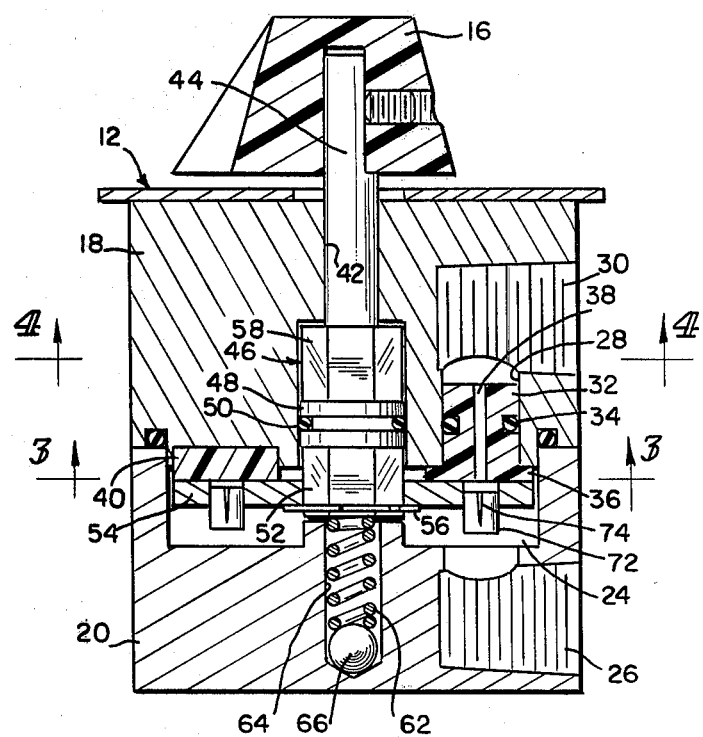
FIG. 2 is an axial section of a control valve for selectively providing a plurality of oxygen flow rates in an oxygen kit as shown in FIG. 1, taken on the line 2—2 of FIG. 3.
Figure 3:
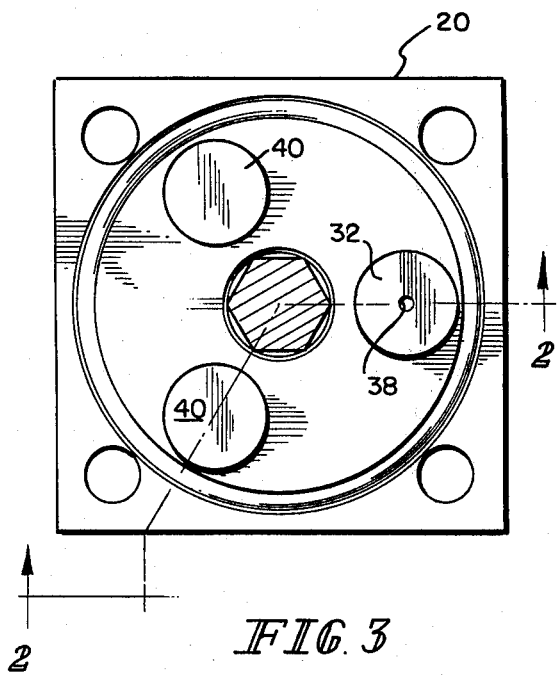
FIG. 3 is an end elevation, taken on the line 3—3 of FIG. 2 showing one part of the valve housing.
Figure 4:
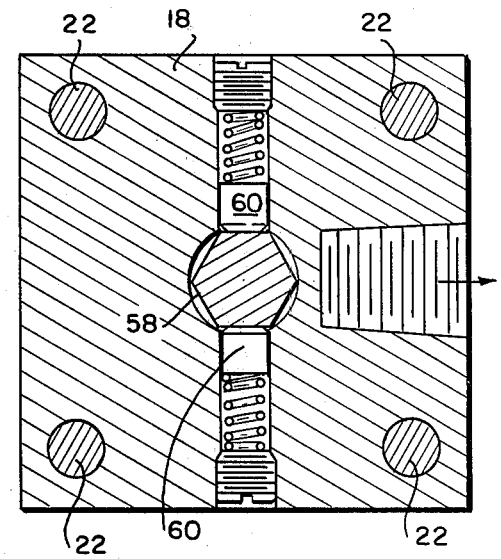
FIG. 4 is a transverse section taken on the line 4—4 of FIG. 2.

In accordance with the present invention, the selective metering control device 12 may be as shown in FIG. 2. Such device comprises a valve housing formed of two parts 18 and 20 secured in assembled relation by bolts 22 at the corners, as shown in FIGS. 3 and 4. The part 20 is formed with an annular cavity forming a gas plenum chamber 24 which receives gas from an inlet opening 26. The housing part 18 contains an eccentric axial bore 28 leading to an outlet 30. The bore 28 is fitted with a valve seat member 32 desirably of a material such as nylon plastic adapted to make sealing engagement with the metering disk mentioned below. This is sealed in the bore 28 by an O-ring 34 and has an end flange 36 bearing against one end wall of the chamber 24. The valve seat member has a central bore 38 of adequate size to pass gas at all metered flow rates. At a plurality of angularly spaced positions, the face of the body part 18 is fitted with a plurality of pressure pads 40 to provide support for the metering disk in a common radial plane with the end face of the valve seat 32.

The body part 18 has a central bore 42 to receive a valve stem 44. Such stem carries a hub 46 having a central cylindrical portion 48 with an annular groove to contain a sealing O-ring 50. The lower end portion 52 of the hub is of hexagonal cross section and receives a metering disk 54 held thereon by a snap ring 56 and adapted to be rotatably driven thereby. The opposite end section 58 of the hub is also of hexagonal cross section as shown in FIG. 4. It is engaged at opposite sides by two flat-ended index pins 60 which are spring pressed toward the hub so as to hold it in six distinct index positions. The pins 60 may be of nylon plastic material.

The hub and spindle assembly is spring pressed axially by a spring 62 housed in the central bore 64 in the body part 20 and supported at its outer end by a hardened ball 66. The axial pressure of the spring 62 presses the metering disk 54 against the valve seat 32 and the pressure pads 40, and the distribution of pressure tends to hold the metering disk normal to the axis of the hub and flat against the end face of the valve seat insert 32, in sealing relation therewith.

Figure 5:
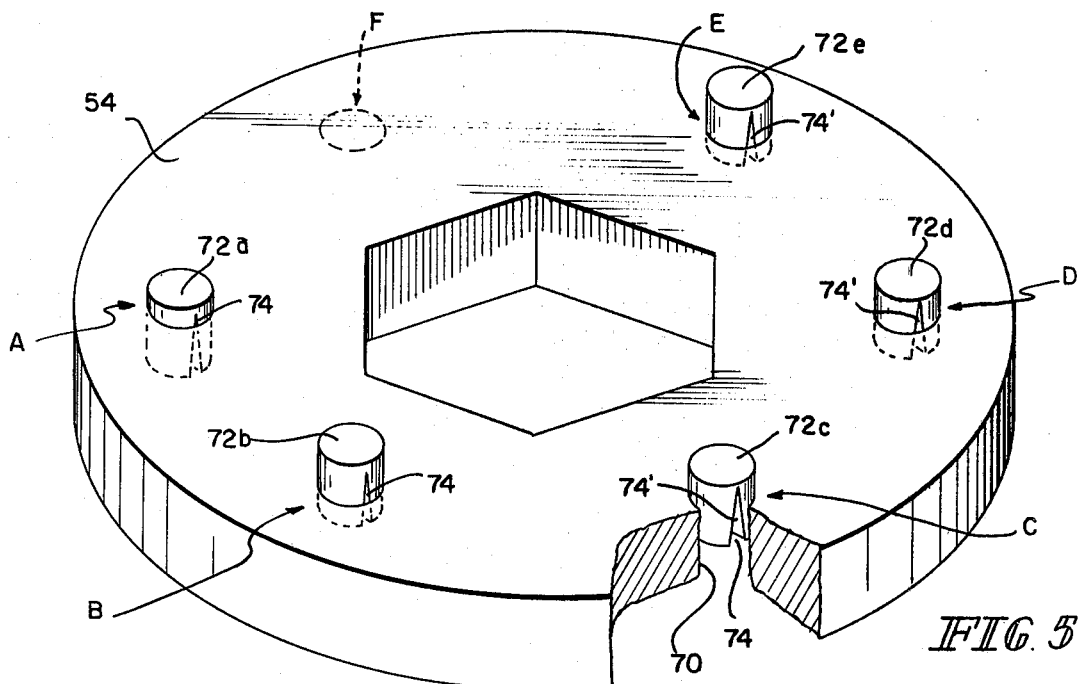
FIG. 5 is a perspective view of a metering disk used in the valve of FIG. 2.
Figure 6:
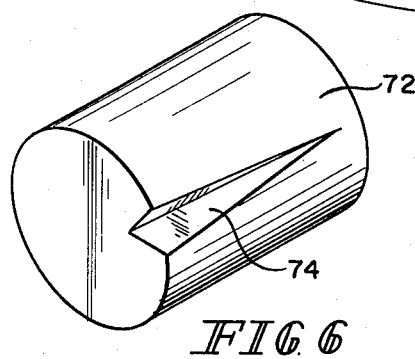
FIG. 6 is a perspective view of a scribed plug used in forming calibrated metering orifices in the metering disk of FIG. 5.

As shown in FIG. 5, the metering disk 54 has five positions A-E provided with metering orifices respectively adapted to be aligned with the valve seat 32 as the hub and spindle assembly is rotated by the knob 16 between five of its six indexing positions. The sixth position F is blank, and provides a no-flow position of adjustment of the control valve 12.

Figure 7:
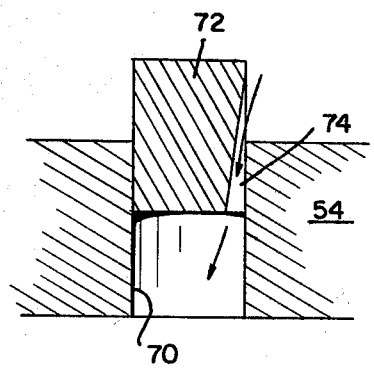
FIG. 7 is a sectional view showing an assembly of the plug of FIG. 6 with the metering disk of FIG. 5.

At each of the orifice positions, a calibrated metering orifice is formed by first drilling a hole 70 and then inserting as by pressing into the hole a tight-fitting plug 72 of conforming cross section and having in its side wall a scribed groove 74 of progressively decreasing cross-sectional area from the lower end of the plug 72 toward its upper end. The scribed groove opens through the bottom end of the plug (as viewed in FIGS. 5 and 7) and preferably terminates short of the upper end of the plug 72. Because of the progressively decreasing cross section of the groove 74, the size of the orifice defined between the walls of that groove and the wall of the hole 70 will depend upon the depth to which the plug 72 is pressed into the hole 70, and that depth can be controlled to control the size of the orifice. Accordingly, the disk can be provided with orifices of progressively increasing size by pressing the plugs 72 into the holes 74 in the disk to different depth. If the full range of orifice sizes desired cannot be provided by varying the depth to which the same plugs 72 are inserted, the smaller orifices can be formed with plugs having scribed grooves of one depth, and larger orifices can be formed by using plugs scribed with grooves of a greater depth. Thus, in FIG. 5, orifices A and B are formed with plugs 72a and 72b, having similar grooves 74, while orifices C, D, and E are formed with plugs 72c, d, and e having similar scribed grooves 74' deeper than the grooves 74 of plugs 72a and b. The holes 70 are conveniently straight-sided cylindrical holes and may be made by conventional drilling operations, and the plugs 72 may be short lengths of cylindrical rod of a size to fit the holes with a self-sustaining fit. By way of example, in a preferred embodiment, the plugs 72 were ⅛ inch in diameter and about 5/32 inch long, and the holes 70 were sufficiently smaller than the plugs 72 to provide a tight press fit. Both the disk and plugs are conveniently made of brass, but other metals such as stainless steel may be used. The scribed grooves 74 and 74' are conveniently formed by a scribing operation with a single-tooth scribing tool. Such grooves are desirably of triangular cross section, for example with a 60° bottom angle. Other cross-sectional shapes may be used. Alternatively, it is feasible to scribe a groove in the wall of the hole and to use a plug having an uninterrupted surface and driving such plug to a position along the wall groove to produce an orifice of the desired flow rate.

Figure 9:
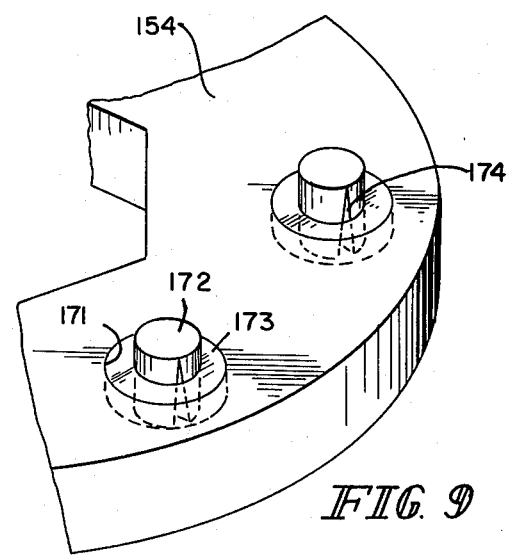
FIG. 9 is a partial perspective view of a metering disk provided with metering orifices shown in FIG. 8.
Figure 8:
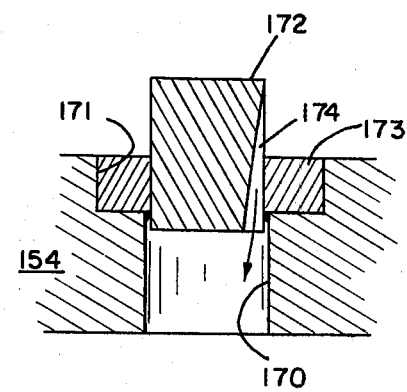
FIG. 8 is a similar sectional view of a modified embodiment of the invention in which the metering orifice is formed between a plug and a ring inserted in the metering disk.

In the modification of FIGS. 8 and 9, instead of forming the orifices directly in holes in the body of a metering disk 154, the metering disk is provided with oversize holes 170 having counterbores 171 at their upper ends, and the calibrated orifices are formed between a ring 173 and a plug 172. Ring and plug assemblies may be formed and calibrated in advance, and selectively inserted in the counterbores 171 of the metering disk 154 to provide the desired flow rates. As in the previous modification, the ring bodies 173 are provided with holes and the plugs 172 have scribed grooves 174 in their side surfaces and are pressed into the ring bodies 173 to calibrated depths that provide openings having cross-sectional areas giving the desired flow rates.

Figure 10:
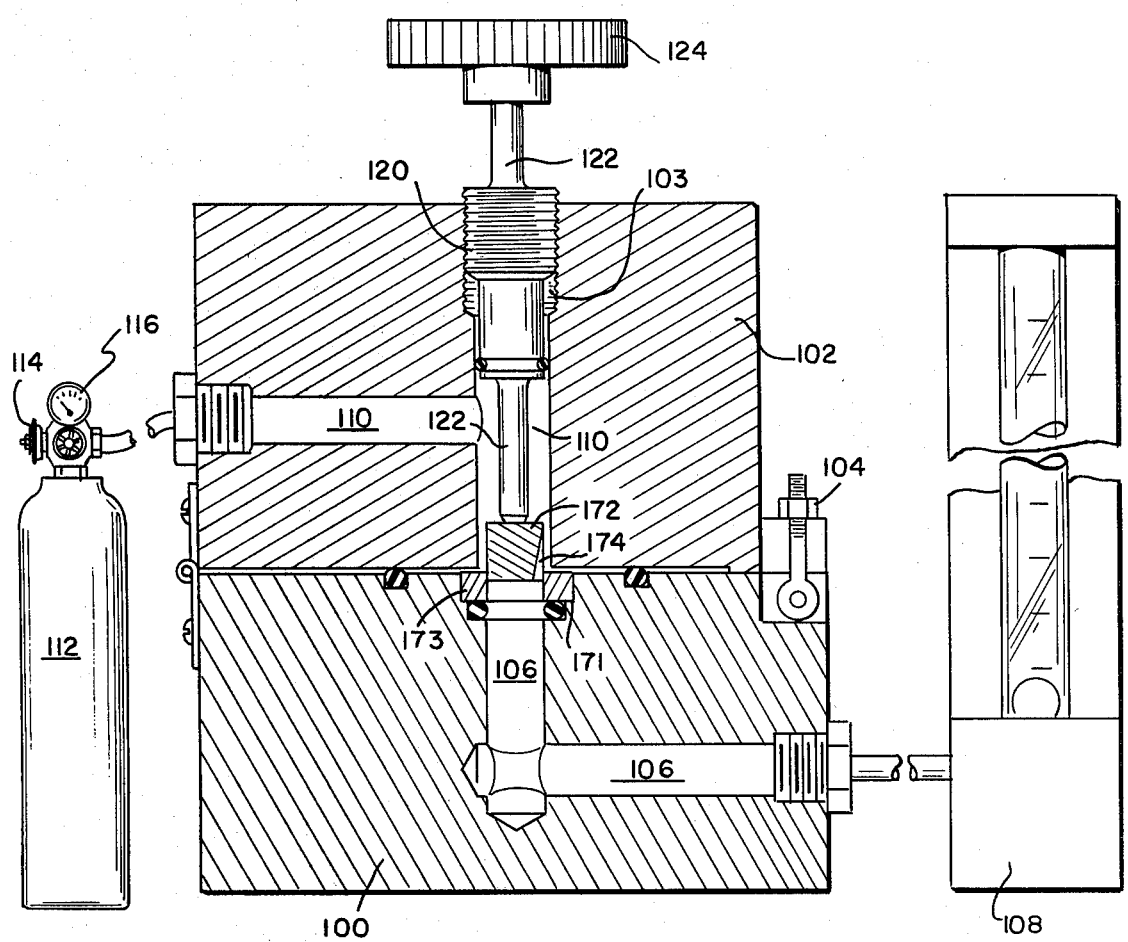
FIG. 10 is a diagrammatic sectional view of apparatus for calibrating a metering orifice of the type shown in FIGS. 8 and 9.

Mechanism for calibrating orifices of the type shown in FIGS. 8 and 9 is shown in FIG. 10. This comprises a clamp base 100 and a hinged cover 102 adapted to be clamped closed by a clamp bolt 104. The base is formed with a central seat 171 for the reception of an orifice ring body 173 with its central opening in communication with an outlet passage 106 connected to a flow meter 108. The cover 102 is provided with an in-flow passage 110 adapted to be connected to an oxygen bottle 112 having a pressure regulator 114 and a pressure meter 116. The upper end of the cover 102 is provided with a threaded opening 103 into which is threaded the enlarged shank 120 of a pressure bar 122 adapted to be manually rotated by a handle 124 to exert pressure on the plug 172 and force it to a progressively increasing depth in the ring 173.

In operation of this calibrating mechanism, oxygen is supplied from the oxygen supply tank 112 at a regulated pressure and flows through the orifice assembly formed by the ring 173 and plug 172. The plug 172 is started into the ring 173 with the large end of its scribed groove 174 downward. As gas flows through the system and through the orifice defined between the walls of that scribed groove 174 and the wall of the hole in the ring 173, the handle 124 on the pressure bar 122 is rotated to press the plug 172 progressively into the ring 173 and thus to progressively decrease the effective cross-sectional area of the orifice defined by the groove 174. Meanwhile, the gas flow rate is monitored on the flow meter 108, and when the desired flow rate is obtained, the pressing of the plug 172 into the ring 173 is stopped so as to leave the plug 172 in a position such that its scribed groove 174 forms an orifice giving the desired flow rate.

Figure 11:
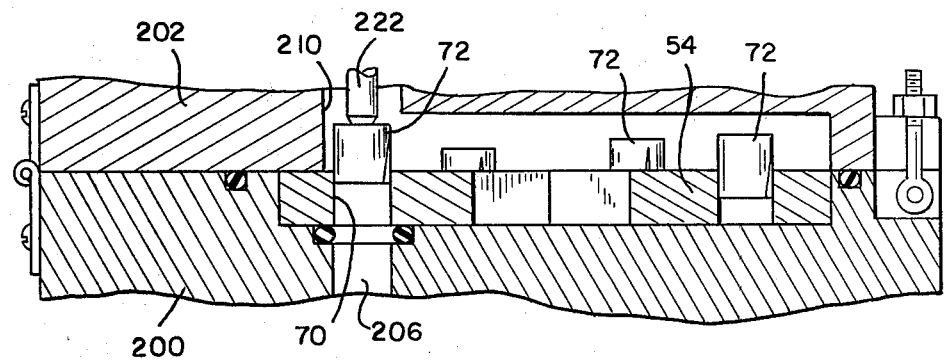
FIG. 11 is a diagrammatic partial section of apparatus for calibrating metering orifices in a disk as shown in FIG. 5.

The orifices in the metering disk 54 of the modification shown in FIGS. 2-7 may be calibrated in an analogous manner in apparatus shown in FIG. 11. The metering disk 54 is clamped between pressure plates 200 and 202 having gas inlet and outlet passages 210 and 206, and oriented with one of its plugs 72 aligned with the pressure bar 222. The plug 72 is pressed into the hole 70 while monitoring the flow rate with a flow meter, and the pressing is stopped when the plug reaches a position which provides an orifice giving the desired flow rates. The plate is then rotated and the calibration repeated for each plug 72.

Operation of the selective control device of FIGS. 2-7 is as follows. The several orifices at positions A-E on the metering disk are calibrated to provide different predetermined gas flow rates, as by the calibration method described above. The metering disk 54 is then mounted in the selective control valve housing as shown in FIG. 2, so that it is pressed by the spring 62 against the valve seat 32 and the pads 40. The metering disk 54 is then rotated by the knob 16 to bring a selected orifice 70-72 into alignment with the valve seat 32. In each case, the selected orifice will provide a predetermined gas flow rate from the inlet 26 into the gas chamber 24 and thence through the opening defined by the scribed groove 74 in the plug 72. The gas passing through the defined orifice will flow through the central bore 38 of the valve seat insert 32 and thence to the outlet 30 from the valve body. When a different flow rate is desired, the knob 16 is indexed to a new position, to bring a different orifice 70-72 into alignment with the valve seat. When no flow is desired, the metering disk can be rotated to bring the no-flow position F into alignment with that valve seat, and the flow will be closed off.

The orifices provided by the present invention can be calibrated under standard pressure and temperature conditions with the calibration mechanism shown in FIG. 10 to give highly precise flow rates for the several indexing positions of the valve of the selective control valve shown in FIGS. 2-7. The relief or scribed groove 74 in the surface of each orifice plug 72, being of progressively decreasing cross-sectional area, can be inserted into its hole 70 to a determined depth which precisely produces an orifice cross-sectional area that gives a desired gas flow rate. Accordingly, the selective control valve will give a series of flow rates which are substantially exact and precise. The user of an oxygen supply kit controlled by a selective control valve in accordance with the present invention will thus accurately receive a quantity of oxygen in accordance with his doctor's prescription.

I claim:

1. A calibrated gas metering valve, comprising
a valve body having a gas inlet and a gas outlet and a dividing wall formed with a hole therein defining a passage for gas flow from the inlet to the outlet,
a plug press-fitted in the hole so as to be solely positioned therein by the fitting engagement of its peripheral surface with the wall of the hole,
one of the interface surfaces between the plug and the wall of the hole having therein a groove or the like of progressively decreasing cross section so as to define therebetween an opening of a size that depends on the depth to which the plug is inserted in the hole,
the plug being positioned in the hole at a determined depth which produces an opening size giving a desired flow rate.

2. A gas metering as in claim 1 in which the plug is positioned in the hole at a depth which produces a calibrated gas flow rate through the valve.

3. A gas metering device as in claim 1 in which the groove is in the surface of the plug.

4. A gas metering device as in claim 1 in which said wall of the valve body contains an insert ring seated therein and defining the hole in which the plug is fitted.

5. A gas metering device comprising
a valve plate,
an insert ring sealingly mounted in the valve plate and forming a valve body with a hole therein,
a plug press-fitted in the hole so as to be positioned therein by the fitting engagement of its peripheral surface with the wall of the hole,
one of the interface surfaces between the plug and the wall of the hole having therein a groove or the like of progressively decreasing cross section so as to define therebetween an opening of a size that depends on the depth to which the plug is inserted in the hole,
the plug being positioned in the hole at a determined depth which produces an opening size giving a desired flow rate so as to form a calibrated orifice in said valve plate.

6. A gas metering element adapted to be selectively moved to a plurality of metering positions for selectively providing a series of different gas flow rates,
a series of straight-sided holes in said element adapted to be selectively positioned to control gas flow through a passage,
a plug press-fitted in each such hole so as to be positioned therein by its engagement in the hole, having in its surface an elongated groove of progressively decreasing cross-sectional area so that the size of the opening depends on the depth to which the plug is positioned in its hole,
the several plugs being positioned in their respective holes at determined depths which produce openings giving a series of different gas flow rates.

7. A gas metering element as in claim 6 in which a plurality of holes contain similar plugs inserted at different depths so as to provide different size openings giving different gas flow rates.

8. A gas metering valve for selectively providing a series of different calibrated gas flow rates therethrough, comprising

- a valve body having a gas chamber therein and a gas inlet thereto,
- a gas outlet and a valve seat defining a gas flow passage from the chamber to the outlet,
- a metering disk mounted in said body and rotatable to bring a plurality of different portions thereof into position to control gas flow through said valve seat,
- each such portion of the disk having a straight-sided hole therein for passing gas to the valve seat,
- and a plug press-fitted in each such hole and having in its surface a groove of progressively decreasing cross section so as to define with the wall of the hole an opening of a size which depends on the depth to which the plug is positioned in its hole,
- the several plugs being positioned in their respective holes at depths to provide a series of different sized holes determined to give a series of different gas flow rates.

9. A gas metering valve as in claim 8 in which said metering disk is mounted for rotation on its axis, said disk having a flat face and being resiliently pressed axially to press its flat face into sealing engagement with the valve seat, and a plurality of pressure pads coplanar with said valve seat and positioned at angularly spaced points about the axis of the metering disk to support the same for rotation in a radial plane.

10. A gas metering valve as in claim 9 in which said plugs are pressed into the holes in the metering disk from the opposite side thereof from said seat-engaging flat side.

11. A selective oxygen metering valve for metering therapeutic oxygen at controlled rates, comprising

- a valve housing having an inlet and outlet and defining a flow passage therebetween,
- a valve seat in said passage,
- a valve disk having a plurality of holes therein to pass gas through said passage and said valve seat, said disk being movable to bring said holes selectively into controlling alignment with said valve seat,
- a plug press-fitted in each such hole and having in its surface a groove of progressively decreasing cross-sectional area to define with the wall of its hole an opening of a size which depends on the depth to which the plug is positioned in its hole,
- the several plugs being positioned at depths to provide a series of different sized holes giving a series of different gas flow rates.

12. A selective oxygen metering valve as in claim 11 which includes openings giving gas flow rates in the range of from one to five liters, of oxygen per minute.

* * * * *

UNITED STATES PATENT AND TRADEMARK OFFICE
CERTIFICATE OF CORRECTION

PATENT NO. : 4,241,896
DATED : December 30, 1980
INVENTOR(S) : Clayton B. Voege

It is certified that error appears in the above-identified patent and that said Letters Patent are hereby corrected as shown below:

Column 6, line 24 (Claim 2, line 1), after "metering" insert --valve--;

line 27 (Claim 3, line 1), change "device" to --valve--; and line 29 (Claim 4, line 1), change "device" to --valve--.

Signed and Sealed this

Twenty-eighth Day of April 1981

[SEAL]

Attest:

RENE D. TEGTMEYER

Attesting Officer

Acting Commissioner of Patents and Trademarks